US011071816B2

(12) United States Patent
Mehta et al.

(10) Patent No.: US 11,071,816 B2
(45) Date of Patent: Jul. 27, 2021

(54) SYSTEM, APPARATUS AND METHOD FOR MONITORING ANTERIOR CHAMBER INTRAOPERATIVE INTRAOCULAR PRESSURE

(71) Applicant: Johnson & Johnson Surgical Vision, Inc., Santa Ana, CA (US)

(72) Inventors: Deep Mehta, Irvine, CA (US); Dung T. Ma, Anaheim, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 93 days.

(21) Appl. No.: 15/725,160

(22) Filed: Oct. 4, 2017

(65) Prior Publication Data

US 2019/0099548 A1    Apr. 4, 2019

(51) Int. Cl.
*A61M 3/02* (2006.01)
*A61F 9/007* (2006.01)
*A61M 1/00* (2006.01)

(52) U.S. Cl.
CPC ....... *A61M 3/0283* (2013.01); *A61F 9/00745* (2013.01); *A61M 1/0031* (2013.01); *A61M 1/0058* (2013.01); *A61M 1/0076* (2013.01); *A61M 3/022* (2014.02); *A61M 3/0216* (2014.02); *A61B 2217/005* (2013.01); *A61B 2217/007* (2013.01); *A61M 2205/15* (2013.01); *A61M 2205/18* (2013.01); *A61M 2205/3334* (2013.01); *A61M 2205/3344* (2013.01); *A61M 2205/3561* (2013.01); *A61M 2205/3592* (2013.01); *A61M 2205/50* (2013.01); *A61M 2205/502* (2013.01); *A61M 2205/505* (2013.01);
(Continued)

(58) Field of Classification Search
CPC ... A61M 3/0283; A61M 3/0216; A61M 3/022
See application file for complete search history.

(56) References Cited

U.S. PATENT DOCUMENTS

| 3,393,566 A | 7/1968 | Green et al. |
| 3,575,301 A | 4/1971 | Panissidi |
| 3,920,014 A | 11/1975 | Banko |

(Continued)

FOREIGN PATENT DOCUMENTS

| DE | 19753636 A1 | 9/1999 |
| EP | 1382291 A2 | 1/2004 |

(Continued)

OTHER PUBLICATIONS

Partial International Search Report for Application No. PCT/IB2018/057580, dated Jan. 23, 2019, 15 pages.

(Continued)

*Primary Examiner* — Emily L Schmidt
*Assistant Examiner* — Leah J Swanson
(74) *Attorney, Agent, or Firm* — Johnson & Johnson Surgical Vision, Inc.

(57) ABSTRACT

A method for maintaining anterior chamber intraoperative intraocular pressure (IOP) is provided by receiving and/or detecting variables of a surgical system and utilizing those variables to monitor intraoperative IOP. Determining an IOP in real time during a surgical procedure either provides a notification to an eye surgeon or allows a target IOP of the anterior chamber of a patient's eye to be set and maintained.

11 Claims, 6 Drawing Sheets

(52) U.S. Cl.
CPC . *A61M 2205/52* (2013.01); *A61M 2210/0612* (2013.01)

(56) References Cited

U.S. PATENT DOCUMENTS

| | | | |
|---|---|---|---|
| 4,274,411 A | 6/1981 | Dotson, Jr. | |
| 4,653,719 A | 3/1987 | Cabrera et al. | |
| 4,702,733 A | 10/1987 | Wright et al. | |
| 4,818,186 A | 4/1989 | Pastrone et al. | |
| 4,832,685 A | 5/1989 | Haines | |
| 4,935,005 A | 6/1990 | Haines | |
| 4,954,960 A | 9/1990 | Lo et al. | |
| 5,032,111 A | 7/1991 | Morris et al. | |
| 5,047,009 A | 9/1991 | Morris et al. | |
| 5,106,367 A | 4/1992 | Ureche et al. | |
| 5,167,620 A | 12/1992 | Ureche et al. | |
| 5,242,404 A | 9/1993 | Conley et al. | |
| 5,354,268 A | 10/1994 | Peterson et al. | |
| 5,405,269 A | 4/1995 | Stupecky | |
| 5,476,448 A | 12/1995 | Urich | |
| 5,487,827 A | 1/1996 | Peterson et al. | |
| 5,569,188 A | 10/1996 | MacKool | |
| 5,591,127 A | 1/1997 | Barwick, Jr. et al. | |
| 5,616,120 A | 4/1997 | Andrew et al. | |
| 5,649,905 A | 7/1997 | Zanger et al. | |
| 5,695,473 A | 12/1997 | Olsen | |
| 5,697,898 A | 12/1997 | Devine | |
| 5,700,240 A | 12/1997 | Barwick, Jr. et al. | |
| 5,733,256 A | 3/1998 | Costin | |
| 5,766,146 A | 6/1998 | Barwick | |
| 5,865,764 A | 2/1999 | Moorhead | |
| 5,885,243 A | 3/1999 | Capetan et al. | |
| 5,910,110 A | 6/1999 | Bastable | |
| 5,935,106 A | 8/1999 | Olsen | |
| 6,050,496 A | 4/2000 | Hefler | |
| 6,159,175 A | 12/2000 | Strukel et al. | |
| 6,167,588 B1 | 1/2001 | Dyson | |
| 6,170,383 B1 | 1/2001 | Mauritz | |
| 6,179,808 B1 | 1/2001 | Boukhny et al. | |
| 6,190,354 B1 | 2/2001 | Sell et al. | |
| 6,423,029 B1 | 7/2002 | Elsberry | |
| 6,491,661 B1 | 12/2002 | Boukhny et al. | |
| 6,533,747 B1 | 3/2003 | Polaschegg et al. | |
| 6,565,535 B2 | 5/2003 | Zaias et al. | |
| 6,579,255 B2 | 6/2003 | Kadziauskas et al. | |
| 6,599,271 B1 | 7/2003 | Easley | |
| 6,648,223 B2 | 11/2003 | Boukhny et al. | |
| 6,740,058 B2 | 5/2004 | Lal et al. | |
| 6,780,166 B2 | 8/2004 | Kanda et al. | |
| 6,986,753 B2 | 1/2006 | Bui | |
| 7,083,591 B2 | 8/2006 | Cionni | |
| 7,297,137 B2 | 11/2007 | Gordon et al. | |
| 7,785,336 B2 | 8/2010 | Staggs | |
| 8,246,580 B2 | 8/2012 | Hopkins et al. | |
| 8,380,126 B1* | 2/2013 | Ma | A61B 5/7475 455/41.2 |
| 8,430,841 B2 | 4/2013 | Claus et al. | |
| 8,523,812 B2 | 9/2013 | Boukhny et al. | |
| 8,715,220 B2 | 5/2014 | Gerg et al. | |
| 9,482,563 B2 | 11/2016 | Calderin et al. | |
| 9,549,851 B2 | 1/2017 | Chon et al. | |
| 9,795,507 B2 | 10/2017 | Hajishah et al. | |
| 9,861,522 B2 | 1/2018 | Sorensen et al. | |
| 10,182,940 B2 | 1/2019 | Chandrakant et al. | |
| 2001/0023331 A1 | 9/2001 | Kanda et al. | |
| 2002/0019607 A1 | 2/2002 | Bui | |
| 2002/0174910 A1 | 11/2002 | Willeke, Jr. et al. | |
| 2003/0006729 A1 | 1/2003 | Raymond | |
| 2003/0050619 A1 | 3/2003 | Mooijman et al. | |
| 2003/0078487 A1 | 4/2003 | Jeffries et al. | |
| 2003/0105437 A1 | 6/2003 | Neubert | |
| 2004/0092921 A1 | 5/2004 | Kadziauskas et al. | |
| 2004/0101445 A1 | 5/2004 | Shvets et al. | |
| 2005/0080375 A1 | 4/2005 | Kadziauskas et al. | |
| 2005/0096593 A1 | 5/2005 | Pope et al. | |
| 2005/0118048 A1 | 6/2005 | Traxinger | |
| 2005/0209621 A1 | 9/2005 | Gordon et al. | |
| 2005/0234441 A1 | 10/2005 | Bisch et al. | |
| 2005/0261628 A1 | 11/2005 | Boukhny et al. | |
| 2005/0261715 A1 | 11/2005 | Boukhny et al. | |
| 2005/0267504 A1 | 12/2005 | Boukhny et al. | |
| 2006/0224107 A1 | 10/2006 | Claus et al. | |
| 2006/0224143 A1 | 10/2006 | Claus et al. | |
| 2006/0281986 A1 | 12/2006 | Orilla et al. | |
| 2007/0227265 A1 | 10/2007 | Sugi et al. | |
| 2008/0033349 A1* | 2/2008 | Suzuki | A61M 1/0058 604/35 |
| 2009/0158855 A1* | 6/2009 | Holden | A61M 1/0031 73/756 |
| 2010/0145302 A1 | 6/2010 | Cull et al. | |
| 2010/0280435 A1 | 11/2010 | Raney et al. | |
| 2011/0284777 A1 | 11/2011 | Pitchford et al. | |
| 2011/0295191 A1 | 12/2011 | Injev | |
| 2011/0313343 A1 | 12/2011 | Milutinovic et al. | |
| 2012/0041362 A1 | 2/2012 | Gerg et al. | |
| 2013/0062543 A1 | 3/2013 | Shiao et al. | |
| 2013/0131578 A1 | 5/2013 | Stalmans et al. | |
| 2013/0150782 A1 | 6/2013 | Sorensen et al. | |
| 2013/0246079 A1 | 9/2013 | Hoffman et al. | |
| 2014/0107459 A1 | 4/2014 | Lind et al. | |
| 2014/0114236 A1 | 4/2014 | Gordon et al. | |
| 2014/0114237 A1 | 4/2014 | Gordon et al. | |
| 2014/0163455 A1 | 6/2014 | Wilson et al. | |
| 2014/0171869 A1 | 6/2014 | Zhang | |
| 2014/0206940 A1 | 7/2014 | Hufford | |
| 2014/0257172 A1 | 9/2014 | Yalamanchili et al. | |
| 2014/0282018 A1 | 9/2014 | Amble et al. | |
| 2014/0323953 A1 | 10/2014 | Sorensen et al. | |
| 2014/0364799 A1 | 12/2014 | Beauvais et al. | |
| 2015/0157501 A1 | 6/2015 | Bourne et al. | |
| 2015/0359666 A1 | 12/2015 | Zacharias | |
| 2016/0346123 A1* | 12/2016 | Koplin | A61M 1/0064 |
| 2017/0022488 A1 | 1/2017 | Bermudez et al. | |
| 2017/0224888 A1 | 8/2017 | Hickey et al. | |
| 2017/0246419 A1 | 8/2017 | Callaghan et al. | |
| 2017/0312431 A1 | 11/2017 | Johnson et al. | |
| 2018/0028359 A1 | 2/2018 | Gordon et al. | |
| 2018/0049920 A1 | 2/2018 | Charles | |
| 2018/0279876 A1 | 10/2018 | Paschalis | |
| 2018/0296738 A1 | 10/2018 | King et al. | |
| 2019/0099526 A1 | 4/2019 | Hajishah et al. | |
| 2019/0133822 A1 | 5/2019 | Banko | |
| 2019/0176557 A1 | 6/2019 | Marking et al. | |
| 2019/0262175 A1 | 8/2019 | Kerkhoff et al. | |
| 2019/0282401 A1 | 9/2019 | Sorensen et al. | |
| 2020/0030147 A1 | 1/2020 | Koplin | |

FOREIGN PATENT DOCUMENTS

| | | |
|---|---|---|
| EP | 1471342 A2 | 10/2004 |
| EP | 1471342 B1 | 8/2009 |
| EP | 2379126 A2 | 10/2011 |
| EP | 2320842 B1 | 6/2012 |
| EP | 2164435 B1 | 8/2012 |
| JP | 62500640 T | 3/1987 |
| JP | 2001161740 A2 | 6/2001 |
| WO | 9945868 A | 9/1999 |
| WO | 0194893 A1 | 12/2001 |
| WO | 03047653 A1 | 6/2003 |
| WO | 04108189 A2 | 12/2004 |
| WO | 04110524 A2 | 12/2004 |
| WO | 05037156 A | 4/2005 |
| WO | 2008030872 A1 | 3/2008 |
| WO | 2011045033 A1 | 4/2011 |
| WO | 2011105909 A1 | 9/2011 |
| WO | 2016122790 A1 | 8/2016 |
| WO | 2016150754 A1 | 9/2016 |
| WO | 2016191665 A1 | 12/2016 |

(56) References Cited

FOREIGN PATENT DOCUMENTS

| WO | 2019068151 A1 | 4/2019 |
|---|---|---|
| WO | 2019115584 A1 | 6/2019 |

OTHER PUBLICATIONS

International Search Report and Written Opinion for Application No. PCT/US20171054602, dated Jan. 2, 2018, 10 pages.
International Search Report and Written Opinion for Application No. PCT/IB2018/057494, dated Dec. 19, 2018, 13 pages.
International Search Report and Written Opinion for Application No. PCT/IB2018/057574, dated Dec. 14, 2018, 16 pages.
International Search Report and Written Opinion for Application No. PCT/IB2018/057689, dated Jan. 24, 2019, 16 pages.
International Search Report and Written Opinion for Application No. PCT/IB2018/057699, dated Jan. 30, 2019, 15 pages.
Cioni R.J., "Evaluating Two Key Safety Advances in the Centurion Vision System", ALCON, Cataract and Refractive Surgery Today, Aug. 2019, 4 pages.
Gopesh T., et al., "Rapid and Accurate Pressure Sensing Device for Direct Measurement of Intraocular Pressure", Translational Vision Science and Technology (TVST), Feb. 2020, vol. 9 (3), Article 28, pp. 1-9.
International Search Report for Application No. PCT/IB2020/059372, dated Dec. 22, 2020, 8 pages.
Miller K.M., et al., Millennialeye, Sep./Oct. 2019, Supplement to Cataract & Refractive Surgery Today, 16 pages.

* cited by examiner

SYSTEM, APPARATUS AND METHOD FOR MONITORING ANTERIOR CHAMBER INTRAOPERATIVE INTRAOCULAR PRESSURE

BACKGROUND

Field of Invention

The present disclosure relates generally to medical apparatuses and methods that provide pressurized infusion of liquids for ophthalmic surgery, and more particularly, to medical apparatuses and methods that require determinable, stable or controlled intraoperative intraocular pressure (IOP) within the anterior chamber of the eye.

Description of Related Art

During ophthalmic surgery, an ophthalmic surgical apparatus is used to perform surgical procedures in a patient's eye. An ophthalmic surgical apparatus typically includes a handheld medical implement or tool, such as a handpiece with a tip and/or sleeve, and operating controls for regulating settings or functions of the apparatus and tool. Operation of the tool requires control of various operating settings or functions based on the type of tool used. Such apparatuses typically include a control module, power supply, an irrigation source, one or more aspiration pumps, as well as associated electronic hardware and software for operating a multifunction handheld surgical tool. The handpiece may include a needle or tip which is ultrasonically driven once placed with the incision to, for example, emulsify the lens of the eye. In various surgical procedures, these components work together in order to, for example, emulsify eye tissue, irrigate the eye with a saline solution, and aspirate the emulsified lens from the eye.

An exemplary type of ophthalmic surgery is phacoemulsification. Phacoemulsification includes making a corneal and/or scleral incision and the insertion of a phacoemulsification handpiece that includes a needle or tip that is ultrasonically driven to emulsify, or liquefy, the lens. A phacoemulsification system typically includes a handpiece coupled to an irrigation source and an aspiration pump. The handpiece includes a distal tip that emits ultrasonic energy to emulsify a crystalline lens within the patient's eye. The handpiece includes one or more irrigation ports proximal to the distal tip and coupled to the irrigation source via an irrigation input line. The handpiece further includes an aspiration port at the distal tip that is coupled to the aspiration pump via an aspiration output line. Concomitantly with the emulsification, fluid from the irrigation source (which may be a bottle or bag of saline solution that is elevated above the patient's eye, to establish positive pressure by gravity, and/or with external pressure source) is irrigated into the eye via the irrigation line and the irrigation port(s). This fluid is directed to the crystalline lens in the patient's eye in order to maintain the anterior chamber and capsular bag and replenish the fluid aspirated away with the emulsified crystalline lens material. The irrigation fluid in the patient's eye and the crystalline lens material is aspirated or removed from the eye by the aspiration pump and line via the aspiration port. In some instances, the aspiration pump may be in the form of, for example, a peristaltic or positive displacement pump. Other forms of aspiration pumps are well known in the art, such as vacuum pumps. In addition, more than one pump or more than one type of pump may be used. Additionally, some procedures may include irrigating the eye and aspirating the irrigation fluid without concomitant destruction, alteration or removal of the lens.

Intraocular pressure (IOP) is the fluid pressure inside the anterior chamber of the eye. In a normal eye, intraocular pressure may vary depending on the time of day, activities of the patient, fluid intake, medications, etc. Intraoperative Intraocular pressure of a patient's eye can fluctuate greatly during an ophthalmic surgery procedure. It is well known the IOP in an anterior chamber of the eye is required to be controlled and maintained during such surgical procedures in order to avoid damage to the patient's eye. For the correct function of the eye and its structure (e.g. shape) and to preserve sharp and undamaged vision, it is very important to maintain the intraoperative IOP.

Different medically recognized techniques have been utilized for ophthalmic surgery, such as phacoemulsification, in order to maintain and control the intraoperative IOP of a patient's eye. In various examples, phacoemulsification may involve combining irrigation, aspiration and emulsification within a single handpiece. The handpiece that is typically controlled electrically in order to, for example, control the flow of fluid through the handpiece and tip. As may be appreciated, during a surgical procedure, the flow of fluid to and from a patient's eye (through a fluid infusion/irrigation system or aspiration/extraction system, for example), the fluid pressure flowing through the handpiece, and the power control over the handpiece, are all critical to the procedure performed. Precise control over aspiration and irrigation to the ocular region is desired in order maintain a desired or optimal intraoperative IOP within the anterior chamber of the eye. Similarly, it may be necessary to maintain a stable volume of liquid in the anterior chamber of the eye, which may be accomplished by irrigating fluid into the eye at the same rate as aspirating fluid and lens material from the eye.

In prior ophthalmic surgical devices, the control and settings of the system may be electronically controlled or modified by use of a computer system, control module and/or a user/surgeon. For instance, the control module may also provide feedback information to a user or surgeon regarding the function and operation of the system, or may also receive input from a user or surgeon in order to adjust surgical settings. A surgeon or user may interface with a display system of the control module during use of the device.

Additionally, a surgeon or user may control or adjust certain aspects of the intraoperative IOP by adjusting various settings or functions of the system. For instance, the irrigation source may be in the form of a suspended or lifted saline bottle or bag, and the surgeon is typically able to adjust the height of the bottle or bag to create a specific head height pressure of the fluid flowing from the bottle or bag. In typical systems, the head height pressure, which is a function of the column height, is the static IOP of the fluid flowing through the patient's eye. Accordingly, the surgeon may be able to indirectly set the static IOP by changing the bottle height to a desired level. However, dynamic IOP is a function of surgical parameters and the surgical environment during surgery. Currently, ophthalmic systems do not provide any means for measuring or predicting dynamic IOP.

A surgeon or user may control or adjust the certain aspects of the intraoperative IOP by adjusting the desired irrigation pressure directly through various methods of pressurized infusion.

SUMMARY

The present invention provides a phacoemulsification surgical handpiece, comprising, a distal end having at least one surgical tool, a proximal end having at least one sensor module communicatively connected to at least one irrigation line and at least one aspiration line, and at least one sensor located within the at least one sensor module and resident in line with one of the at least one irrigation line, the at least one aspiration line, and the at least one surgical tool; and at least one communication module communicatively coupled to the at least one sensor module configured to communicate data indicative of ones of the at least one sensor to a surgical console.

The present invention also provides a method for controlling pressure within a surgical system. The method comprises providing a surgical system, which comprises at least one computing processor capable of accessing code from at least one computing memory associated with the at least one computing processor, the processor in communication with a phacoemulsification surgical handpiece, receiving from the phacoemulsification surgical handpiece data from at least one sensor located in line with the proximate end of the phacoemulsification surgical handpiece and the surgical system, and regulating the pressure of at least one fluid line communicatively coupled to the surgical system and the phacoemulsification surgical handpiece in accordance with data from the at least one sensor.

BRIEF DESCRIPTION OF THE DRAWINGS

The organization and manner of the structure and function of the disclosure, together with the further objects and advantages thereof, may be understood by reference to the following description taken in connection with the accompanying drawings, and in which.

DETAILED DESCRIPTION

The following description and the drawings illustrate specific embodiments sufficiently to enable those skilled in the art to practice the described system and method. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

A system and method for receiving and/or detecting certain variables of a surgical system and utilizing those variables to predict an intraoperative intraocular pressure (IOP) and/or determine an IOP in real time during a surgical procedure to either provide a notification to a surgeon or allow a target IOP of the anterior chamber of a patient's eye to be set and maintained which can be applied to any type of system, are disclosed herein.

As discussed herein, a stable intraoperative IOP may be of critical importance in order to maintain a stable anterior chamber pressure during phacoemulsification. A stable intraoperative IOP may be a function of fluid inflow and outflow such that the volume, and in turn the pressure of anterior chamber, remains stable when a chamber is at or near equilibrium.

Embodiments of a subsystem and method will be discussed herein with a particular emphasis on a medical or hospital environment where a surgeon or health care practitioner performs. For example, an embodiment is a phacoemulsification surgical system that comprises an integrated high-speed control module for a phacoemulsification or vitrectomy handpiece that is configured to be inserted into a patient's eye during the phacoemulsification procedure. The system may further comprises one or more sensor(s) to detect variables about the function and operation of the system, such as the rate of fluid flow before and after the fluid flows through the handpiece, and a processor that can collect such variables and/or receive additional variables as inputs from a user.

Figure 1:
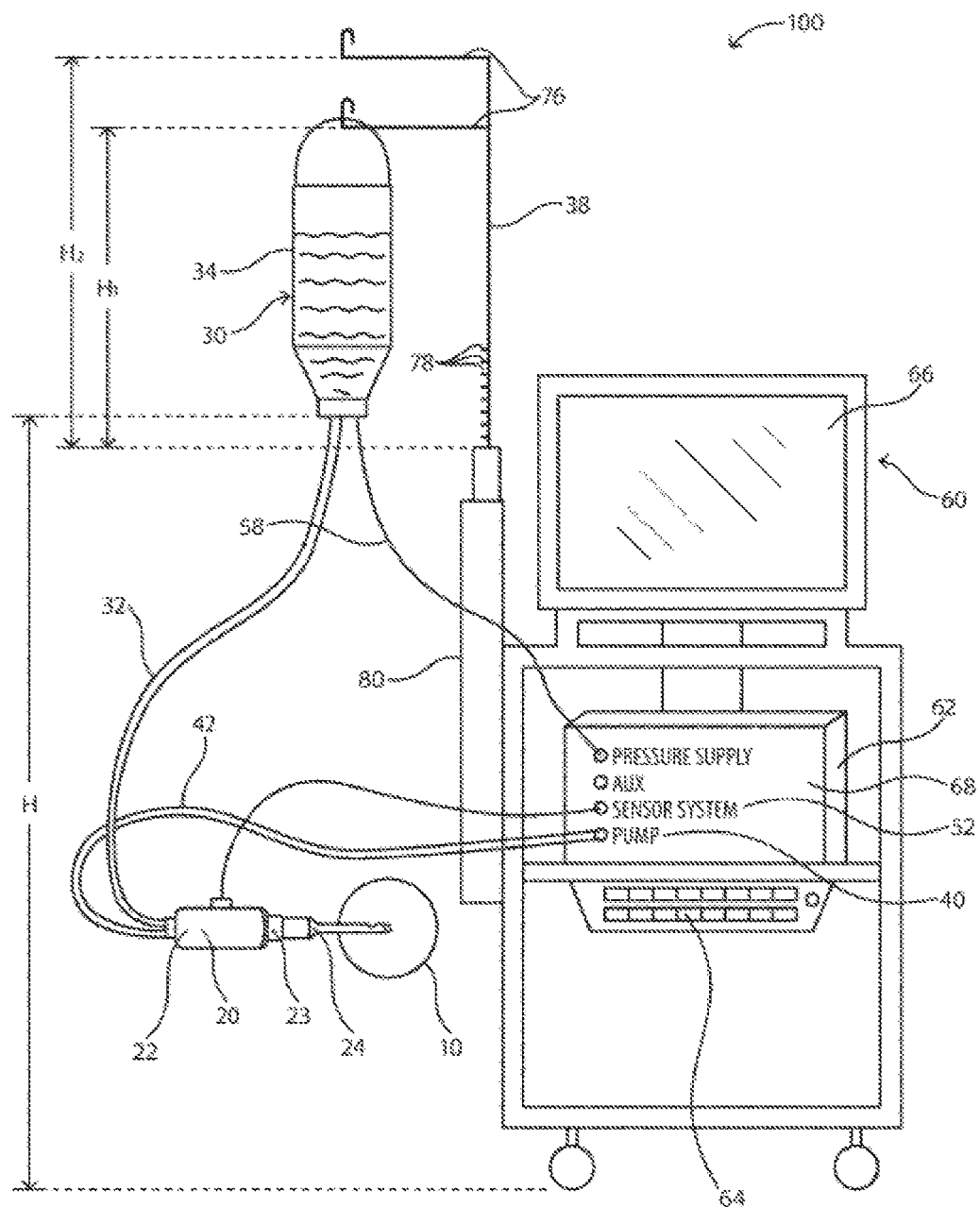
FIG. 1 illustrates a diagram of an exemplary phacoemulsification/diathermy/vitrectomy system in accordance with the present disclosures, the system including a control module to control various features of the system.
Figure 2:
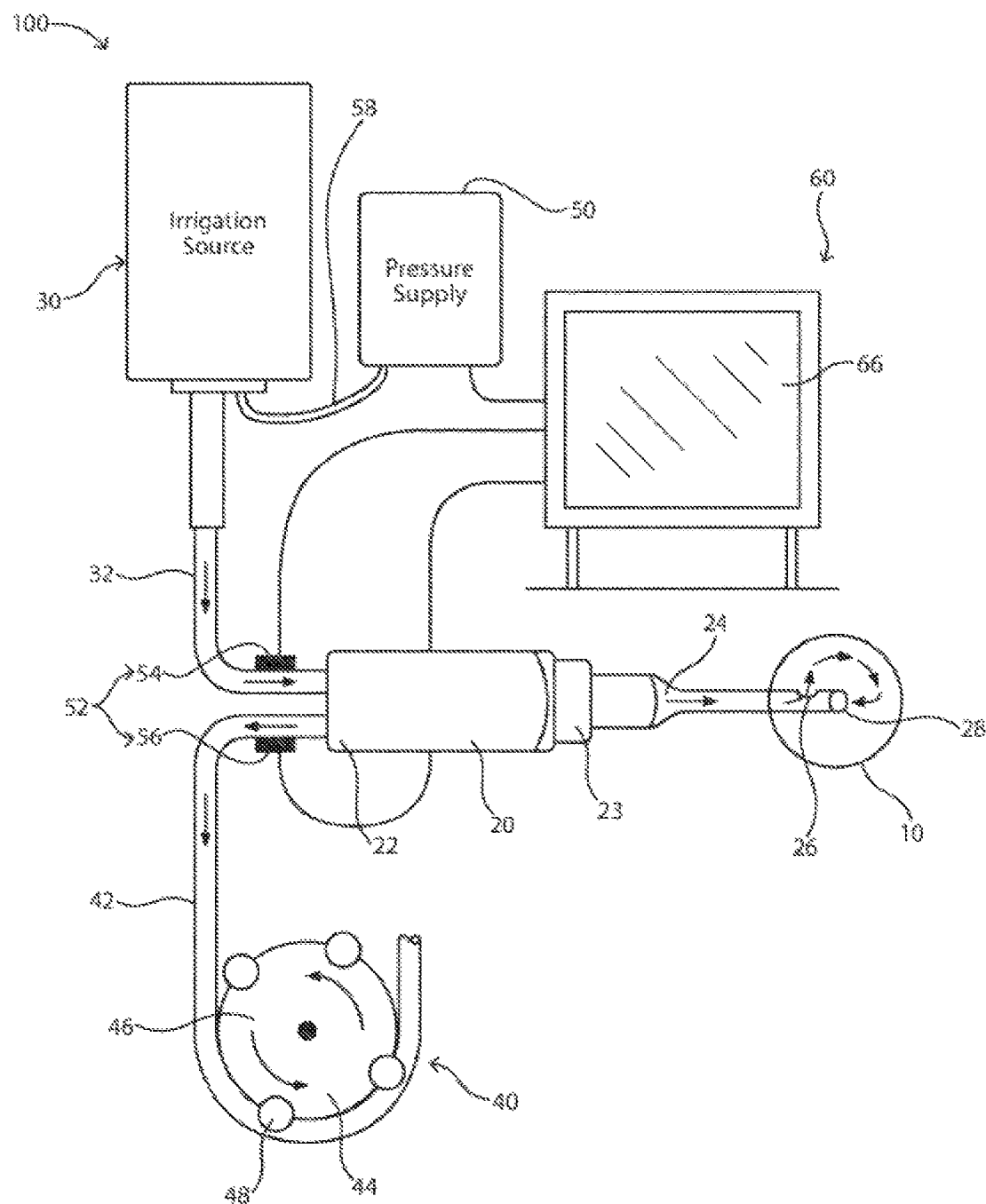
FIG. 2 illustrates an alternative phacoemulsification/diathermy/vitrectomy system and illustrated connected to various components of the system in order to determine characteristics or features of the components.

FIGS. 1 and 2 illustrate an exemplary phacoemulsification/diathermy/vitrectomy system 100. As illustrated, the system 100 includes, for example, a handpiece or wand 20, an irrigation source 30, an aspiration source 40, an optional pressure supply 50, and a control module 60. In illustrative embodiments, fluid is controllably directed through the system 100 in order to irrigate a patient's eye, illustrated representatively at 10, during an ocular surgical procedure. Various embodiments of the handpiece 20, irrigation source 30, aspiration source 40, optional pressure supply 50 and control module 60 are well known in the art and are embodied in this disclosure.

As illustrated in FIG. 2, the irrigation source 30 is configured to supply a predetermined amount of fluid to the handpiece 20 for use during a surgical operation. Such fluid is supplied in order to, for example, stabilize or maintain a certain IOP in the anterior chamber of the eye during surgery, as well as provide means for fluidly transporting any particles (e.g. lens particulates that are created during emulsification) out of the eye. Various aspects (e.g. the flow rate, pressure) of fluid flow into and out of the anterior chamber of the eye will typically affect the operations of the surgical procedure and in particular the IOP measurements of the anterior chamber of the eye during the surgical procedure.

In illustrative embodiments, fluid may flow from the irrigation source 30 to the handpiece 20 via an irrigation line 32. The irrigation source 30 may be any type of irrigation source 30 that can create and control a constant fluid flow. In illustrative embodiments, the irrigation source is elevated to a predetermined height via an extension arm 38. In illustrative embodiments, the irrigation source 30 may be configured to be an elevated drip bag 34 that supplies a steady state of fluid to the irrigation line 32. The pressure supply 50 may be coupled to the irrigation source 30 via line 58 in order to maintain a constant pressure in the irrigation source 30 as fluid exits the irrigation source 30, as is known in the industry. Other embodiments of a uniform irrigation source are well known in the art.

During the surgical procedure, it is typically necessary to remove or aspirate fluid and other material from the eye. Accordingly, fluid may be aspirated from the patient's eye, illustrated representatively at 10, via the handpiece 20 to flow through an aspiration line 42 to the aspiration source 40. The aspiration source 40 may be any type of aspiration source 40 that aspirates fluid and material from the eye. In illustrative embodiments, the aspiration source 40 may be configured to be a flow-based pump 44 (such as a peristaltic pump) or a vacuum-based pump (such as a Venturi pump) that are well known in the art. The aspiration source 40 may create a vacuum system to pump fluid and/or material out of the eye via the aspiration line 42. Other embodiments of an aspiration source are well known in the art.

The handpiece 20 includes a first end 22 and a second end 23. In various embodiments, the second end 23 may be configured to receive an interchangeable tip 24.

The irrigation port 26 is fluidly coupled to the irrigation line 32 to receive fluid flow from the irrigation source 30, and the aspiration port 28 is fluidly coupled to the aspiration line 42 to receive fluid and/or material flow from the eye. The handpiece 20 and the tip 24 may further emit ultrasonic energy into the patient's eye, for instance, to emulsify or break apart the crystalline lens within the patient's eye. Such emulsification may be accomplished by any known methods in the industry, such as, for example, a vibrating unit (not shown) that is configured to ultrasonically vibrate and/or cut the lens, as is known in the art. Other forms of emulsification, such as a laser, are well known in the art. Concomitantly with the emulsification, fluid from the irrigation source 30 is irrigated into the eye via the irrigation line 32 and the irrigation port 26. During and after such emulsification, the irrigation fluid and emulsified crystalline lens material are aspirated from the eye by the aspiration source 40 via the aspiration port 28 and the aspiration line 42. Other medical techniques for removing a crystalline lens also typically include irrigating the eye and aspirating lens parts and other liquids. Additionally, other procedures may include irrigating the eye and aspirating the irrigating fluid within concomitant destruction, alternation or removal of the lens.

The aspiration source 40 is configured to aspirate or remove fluid and other materials from the eye in a steady, uniform flow rate. Various means for steady, uniform aspiration are well known in the art. In illustrative embodiments, the aspiration source 40 may be a Venturi pump, a Peristaltic pump, or a combined Venturi and Peristaltic pump. In illustrative embodiments, and as shown in FIG. 2, a peristaltic pump 44 may be configured to include a rotating pump head 46 having rollers 48. The aspiration line 42 is configured to engage with the rotating pump head 46 as it rotates about an axis. As the pump head 46 rotates the rollers 48 press against the aspiration line 42 causing fluid to flow within the aspiration line 42 in a direction of the movement for the rollers 48. Accordingly, the pump 44 directly controls the volume or rate of fluid flow, and the rate of fluid flow can be easily adjusted by adjusting the rotational speed of the pump head 46. Other means of uniformly controlling fluid flow in an aspiration source 40 are well known in the art. When the aspiration source 40 includes a combined Venturi and Peristaltic pump, the aspiration source 40 may be controlled to automatically switch between the two types of pumps or user controlled to switch between the two types of pumps.

In illustrative embodiments, the control module 60 is configured to monitor and control various components of the system 100. For instance, the control module 60 may monitor, control, and provide power to the pressure supply 50, the aspiration source 40, and/or the handpiece 20. The control module 60 may be in a variety of forms as known in the art. In illustrative embodiments, the control module 60 may include a microprocessor computer 62, a keyboard 64, and a display or screen 66, as illustrated in FIGS. 1 and 2. The microprocessor computer 62 may be operably connected to and control the various other elements of the system, while the keyboard 64 and display 66 permit a user to interact with and control the system components as well. In an embodiment, a virtual keyboard on display 66 may be used instead of keyboard 64. In illustrative embodiments, the control module 60 may also include a pulsed ultrasonic power source (not shown) that can be controlled by the computer 62 in accordance with known methods or algorithms in the art. A system bus 68 may be further provided to enable the various elements to be operable in communication with each other.

The screen 66 may display various measurements, criteria or settings of the system 100—such as the type of procedure, the phase of the procedure and duration of the phase, various parameters such as vacuum, flow rate, power, and values that may be input by the user, such as bottle height or infusion pressure, sleeve size, tip size, vacuum rate, etc. The screen 66 may be in the form of a graphical user interface (GUI) associated with the control module 60 and utilizing a touch-screen interface, for example. The GUI may allow a user to monitor the characteristics of the system 100 or select settings or criteria for various components of the system. For instance, the GUI may permit a user to select or alter the maximum pressure being supplied by the pressure supply 50 to the irrigation source 30. The user may further control the operation of the phase of the procedure, the units of measurement used by the system 100, or the height of the irrigation source 30, as discussed below. The GUI may further allow for the calibration and priming of the pressure in the irrigation source 30.

In illustrative embodiments, the system 100 may include a sensor system 52 configured in a variety of ways or located in various locations. For example, the sensor system 52 may include at least a first sensor or strain gauge 54 located along the irrigation line 32 and a second sensor or strain gauge 56 located along the aspiration line 42, as illustrated in FIG. 2. Other locations for the sensors 54 and 56 are envisioned anywhere in the system 100, e.g., on the handpiece 20, and may be configured to determine a variety of variables that may be used to determine intraoperative IOP measurements in the eye, as discussed below. This information may be relayed from the sensor system 52 to the control module 60 to be used in the determination of IOP measurements.

One factor for consideration in the determination of IOP measurement is the bottle height of the irrigation source 30. As illustrated in FIG. 1, the irrigation source 30 is typically elevated to a predetermined height H. This predetermined elevation may be accomplished by any known means. For example, the irrigation source 30 may be connected to one or more fixed supports 76 on the extension arm 38, the fixed supports spaced at varying heights H1 and H2 along the extension arm 38 to permit the irrigation source 30 to hang down via the force of gravity and place the exit port of the irrigation source 30 at predetermined height H. Alternatively, the extension arm 38 may be retractable (or movable) relative to a fixed receiver 80, the extension arm 38 including biased retaining members 78 that can engage with an aperture (not shown) of the fixed receiver 80 to maintain the extension arm 38 in a relative position with respect to the fixed receiver 80. In such an embodiment, the height H of the exit port of the irrigation source 30 (with respect to the ground) may be maintained in the predetermined position based on the specific retaining member 78 engaging with the aperture of the fixed receiver 80, as is known in the art. Other means of height adjustment are known in the art.

Those of skill in the art will recognize that any step of a method described in connection with an embodiment may be interchanged with another step without departing from the scope of the invention. Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed using a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Any options available for a particular medical device system may be employed with the present invention. For example, with a phacoemulsification system the available settings may include, but are not limited to, irrigation, aspiration, vacuum level, flow rate, pump type (flow based and/or vacuum based), pump speed, ultrasonic power (type and duration, e.g. burst, pulse, duty cycle, etc.), irrigation source height adjustment, linear control of settings, proportional control of settings, panel control of settings, and type (or "shape") of response.

In illustrative embodiments, the interface provides feedback to the user should the predetermined or automatic settings, variables, or criteria need adjustment to ensure all the desired settings of the system. The interface can then permit the user to change or modify those settings accordingly.

Other mechanisms for setting and/or programming a particular setting may be employed with the present invention, including, but not limited to, clicking on an icon on a display screen using a mouse or touch screen, depressing a button/switch on a foot pedal, voice activated commands and/or combinations thereof.

In an embodiment of the present invention, irrigation pressure and/or aspiration vacuum at, or in near proximity to, the phacoemulsification hand piece may be measured in real time. Existing phacoemulsification handpieces do not provide a method to measure pressure on or within the irrigation and/or aspiration lines. Measuring pressure on the irrigation and/or aspiration lines in close proximity to the phacoemulsification handpiece may allow for more accurate and precise estimation of the pressure at the surgical site, such as in, for example, a patient's anterior chamber of the eye. More accurate pressure and vacuum measurements, for example, may be utilized to develop algorithms to provide more robust fluidics control during phacoemulsification surgery which may lead to the improvement of anterior chamber stability. This, in turn, may provide additional comfort to the patient, control over the surgical parameters to the operating surgeon, and ensure safer operation of peristaltic and/or Venturi based pumps during phacoemulsification surgery.

In an embodiment of the present invention, an in-line irrigation pressure sensor and aspiration vacuum sensor may be located on or proximate to the hand piece may provide real-time irrigation and aspiration vacuum data. The proximity of pressure sensors to the surgical site during phacoemulsification surgery may allow for increased monitoring of, for example, the anterior chamber environment. Data collected from one or more of the sensors may allow for the development of an algorithm which may be used to monitor intraocular pressure, and predict occlusion and post occlusion surge events during surgery more accurately and in a more timely manner than is currently available. Using the developed algorithm, discussed herein below, the system may adjust the irrigation and/or aspiration rates in order to improve, for example, anterior chamber stability. Similarly, when the aspiration slows down, fluid circulation may recede and the heat generated from the handpiece tip may damage the eye's tissues, which is not desirable.

Figure 3:
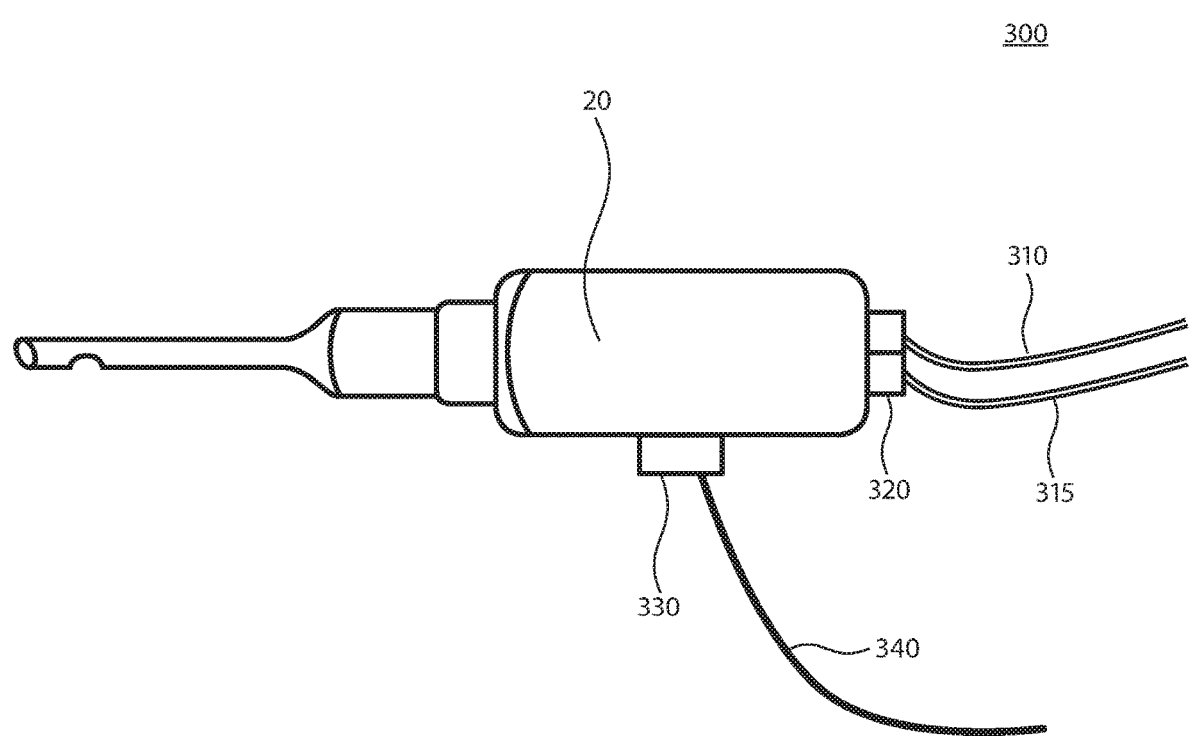
FIG. 3 illustrates an alternative aspect of the phacoemulsification/diathermy/vitrectomy system.

As illustrated in system 300 of FIG. 3, at least one sensor module 320 may be placed in proximity to the phacoemulsification hand piece. Such a module may include a pressure sensor in communication with irrigation line 310 as well as a pressure sensor in communication with the aspiration line 315. The sensor module 320 may receive power and transmit sensor measurement data over power and data pins located in the communication module 330 located on the handpiece 20. The communication module 330 may operate on a specific voltage, for example, and may transmit measurements to the console and or system via a wireless or wired connection.

As illustrated in FIG. 3, the module may receive power from the console or other aspect associated with the console through cable 340 and may similarly transmit data through cable 340. In an embodiment of the present invention, the handpiece system 300 may transmit sensor and other data wirelessly through communication module 330 via any known wireless communication means to a desired portion of the surgical console or system (not shown), such as, for example, via a dedicated wireless method such as Bluetooth Low Energy (BLE), Near Field Communications (NFC) or Wi-Fi technologies.

In an embodiment of the present invention, power to the phacoemulsification hand piece sensor module may be provided through a coin cell battery or like power source which may eliminate the need for cable 340. In such an embodiment, the lack of cable 340 may require the use of wireless communications through communication module 330, as discussed above, and may allow for a less cumbersome use of the handpiece 20. In an embodiment, communication module 330 may be part of sensor module 320.

A steady and inflated anterior eye chamber may allow the surgeon to perform a more successful phacoemulsification procedure for cataract lens extraction and IOL insertion than otherwise possible with a high variance of pressure in the anterior chamber of the patient's eye. The intraoperative pressure in the anterior chamber of the eye is a function of irrigation pressure, aspiration vacuum, and wound leakage. Variation of the anterior chamber pressure may come from the mismatch of sudden aspiration vacuum surge with unmet irrigation inflow, for example. The variation of the anterior chamber pressure causes instability and is not desirable during cataract lens extraction.

A typical method to provide a steady irrigation pressure is to hang a BSS bottle on an IV pole, or to pressurize the source BSS with additional pressure such as air or mechanical force, and connect the BSS via a tube to the irrigation port of the handpiece. The irrigation flow rate to the anterior chamber is then determined by the source pressure and the irrigation line resistance. The aspiration vacuum used may be generated by Peristaltic pump or a Venturi vacuum source downstream from the handpiece aspiration port via a second tube. The aspiration vacuum level may be determined by the Peristaltic vacuum setting the Venturi vacuum setting, and/or one or more pressure or flow sensors. The aspiration vacuum may vary when operating in phacoemulsification mode when certain cataract material being removed from the anterior chamber partially or fully blocks the handpiece tip, also known as an occlusion event.

During an occlusion event, the vacuum continues to build up in the aspiration line, while the aspiration flow rate is reduced or stopped. Occasionally, the occlusion breaks free and the stored energy in the aspiration line is applied to the anterior chamber and suddenly pulls fluid from the anterior chamber resulting in a surge of outflow. When the irrigation inflow is substantially less than the aspiration out flow, the anterior chamber pressure will be less than steady state. More specifically, the anterior chamber pressure may be much lower than atmospheric pressure level, for example. Under such a condition, the anterior chamber may soften and become shallow, or in severe condition, may collapse.

Current phacoemulsification systems, both based on Peristaltic and Venturi systems do not provide suitable methods of maintaining intraoperative IOP during post occlusion surge, often resulting in uncontrolled changes to the stability of the anterior chamber. More specifically, current Venturi based systems, including those using a gravity based infusion system, do not provide any indication(s) relative to post occlusion surge events. For example, if a phacoemulsification needle tip is occluded with cataract material, a high vacuum state may be created within the outflow tubing. This high vacuum level may at least partially collapse the walls of the elastic tubing, and, once the occlusion breaks, the walls of the tubing may rebound back into shape, rapidly pulling fluid from the eye and creating a surge. Because the volume of the anterior and posterior chambers are so small, a slight collapse in the length of the long outflow tubing may create a significant surge and increase the risk for collapse of the eye and aspiration of the posterior capsule during surgery. Thus, the management and quantification of intraoperative IOP and occlusion, and post occlusion surge detection, may provide improved fluidics control during phacoemulsification surgery and may lead to better surgical outcomes by improving anterior chamber stability and more reliable surgical systems.

In an embodiment of the present invention, methods for maintaining IOP may include pressurized infusion, occlusion and post occlusion surge detection, and IOP control.

More specifically, the present invention may utilize in-line irrigation and aspiration pressure sensors, as discussed above, to provide a more accurate and real-time measurement of system pressures nearer the surgical site. Such measurements, along with foot pedal position and bottle height (or specific irrigation pressure, for example), may provide inputs into certain algorithms (discussed in more detail herein) for control of system fractions.

For example, the present invention may increase infusion pressure (irrigation) or reduce the aspiration flow and/or vacuum upon the detection of a post occlusion surge event. Each of these aforementioned elements may be used to improve intraoperative IOP management throughout surgery. For example, using a pressurized irrigation source with the present invention may provide the capability of quickly increasing and/or decreasing irrigation pressure to maintain anterior chamber stability during post occlusion surge events, for example.

The present invention includes intraoperative pressure management algorithms which may incorporate at least some portion of measurable attributes associated with phacoemulsification surgery. Measurable attributes may include patient eye level and wound leakage calibration, intraocular pressure changes during aspiration outflow, occlusion and post occlusion surge detection and mitigation actions, balanced salt solution (BSS) usage, and irrigation and aspiration line block detection, for example.

Figure 4:
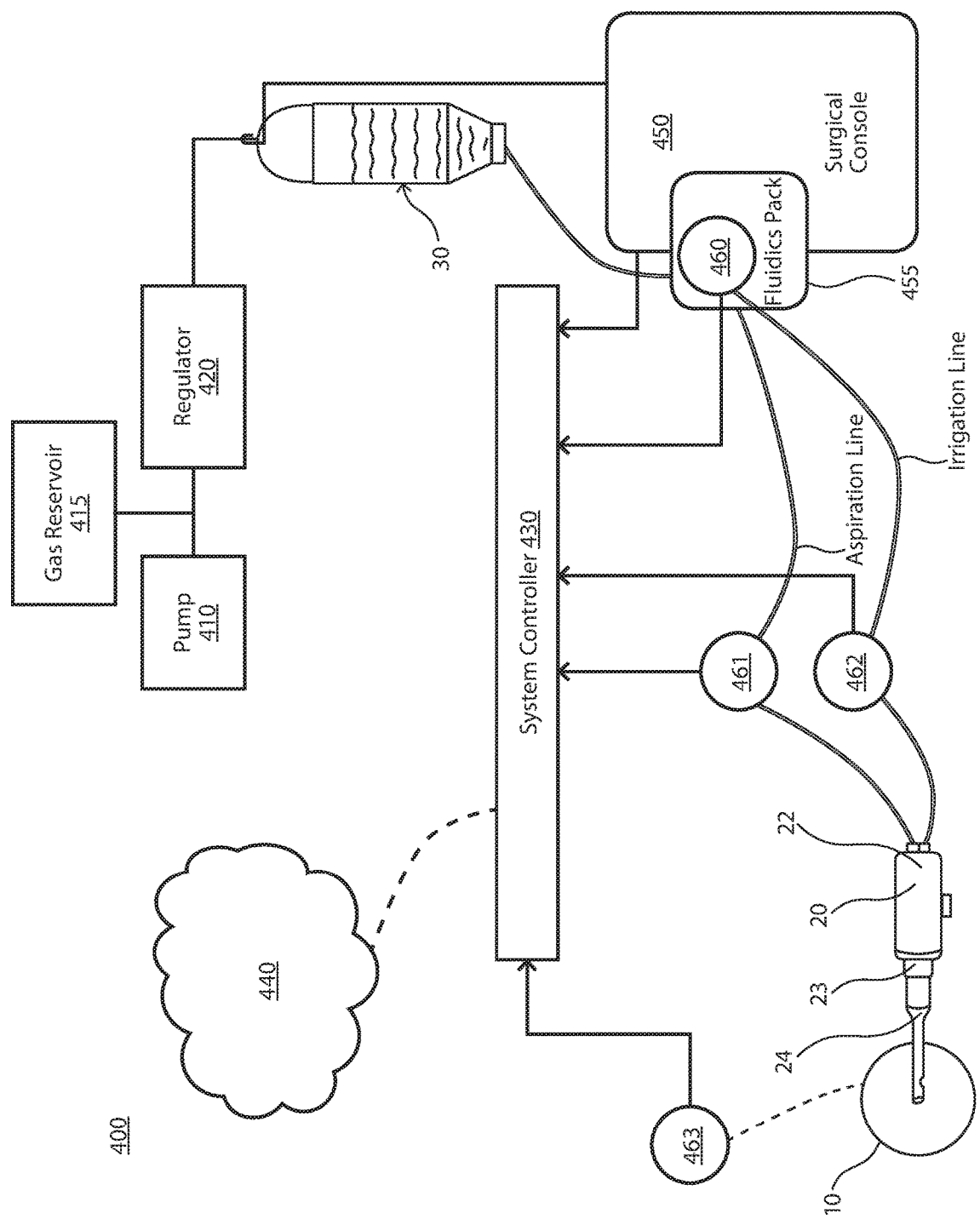
FIG. 4 illustrates an alternative phacoemulsification/diathermy/vitrectomy system and illustrated connected to various components of the system in order to determine characteristics or features of the components.

In an embodiment of the present invention, a plurality of pressure sensors may be used within a surgical system and may provide data which may be used to control aspects of the surgical system. A system level architecture and sensor placement of the present invention is illustrated in FIG. 4. In system 400, surgical console 450 may be in communication with irrigation source 30 and handpiece 20, for example. Surgical console 450 may also be in communication with pump 410, gas reservoir 415, and/or pressure regulator 420, each of which may be used for pressurized irrigation. Surgical console 450 may also be in communication with fluidics pack 455 and system controller 430, which may additionally be in communication with an intranet/internet 440.

Within system 400, an irrigation pressure sensor 462 may be located in close proximity to and/or be coupled to handpiece 20. Similarly, aspiration pressure/vacuum sensor 461 may be located in close proximity to and/or be coupled to handpiece 20. In an embodiment of the present invention, the aspiration pressure/vacuum sensor 461 may be used alone to provide substantially the same improvement in measurements. An additional sensor 463 may be located on the handpiece 20 and may be used to determine intraoperative IOP measurements in the eye. As described herein, the use of one or more pressure sensors may provide improved real-time measurements of patient eye level and wound leakage.

As used herein, "patient eye level" is defined as the height difference between the patient's eye and the fluidics pack where irrigation and aspiration lines are terminated. This height difference may result in a certain amount of pressure inside the anterior chamber. As would be understood by those skilled in the art, a handpiece with the appropriate tip/sleeve and irrigation/aspiration lines would be inserted in the patient's eye through an incision in the anterior chamber. "Wound leakage", as used herein, is defined as the fluid out flow from the anterior chamber during surgery through the incision site. The amount of fluid out flow and related pressure changes inside the chamber may be a function of incision size.

The irrigation pressure sensor 462 and aspiration pressure/vacuum sensor 461, may each be located at the handpiece 20 and may be able to measure the pressure changes inside the anterior chamber due to patient eye level and wound leakage given close proximity of the sensors to the anterior chamber. In an embodiment of the present invention, during the prime/tune of surgical console 450, the system 400 may perform an initial patient eye level calibration by storing pressure measurements taken by sensor 461 and sensor 462. Similarly, subsequent measurements may be taken by sensor 461 and sensor 462 and stored when the handpiece 20 is inserted into the anterior chamber while there is no aspiration out flow.

As will be appreciated by those skilled in the art, intraoperative pressure may change inside the anterior chamber during aspiration outflow. In an embodiment of the present invention, a surgeon may program surgical console 450 to establish a desired intraoperative pressure prior to the start of surgery. When handpiece 20 is inserted into the anterior chamber of the eye 10, the intraoperative pressure management algorithm may take one or more measurements from the irrigation pressure sensor 462, for example, and compare the obtained value to the desired pressure value contained in the console 450 and/or stored in system controller 430. If, for example, the irrigation pressure sensor 462 measurement is higher than the desired pressure, then the algorithm may reduce the irrigation pressure by commanding the pressure regulator 420 to vent excess pressure until the irrigation pressure is substantially equal to the desired pressure. If, for example, the irrigation pressure measurement is lower than the desired pressure, then the algorithm may increase the irrigation pressure by commanding the pressure regulator 420 to increase pressure until the irrigation pressure is substantially equal to the desired pressure.

Figure 5:
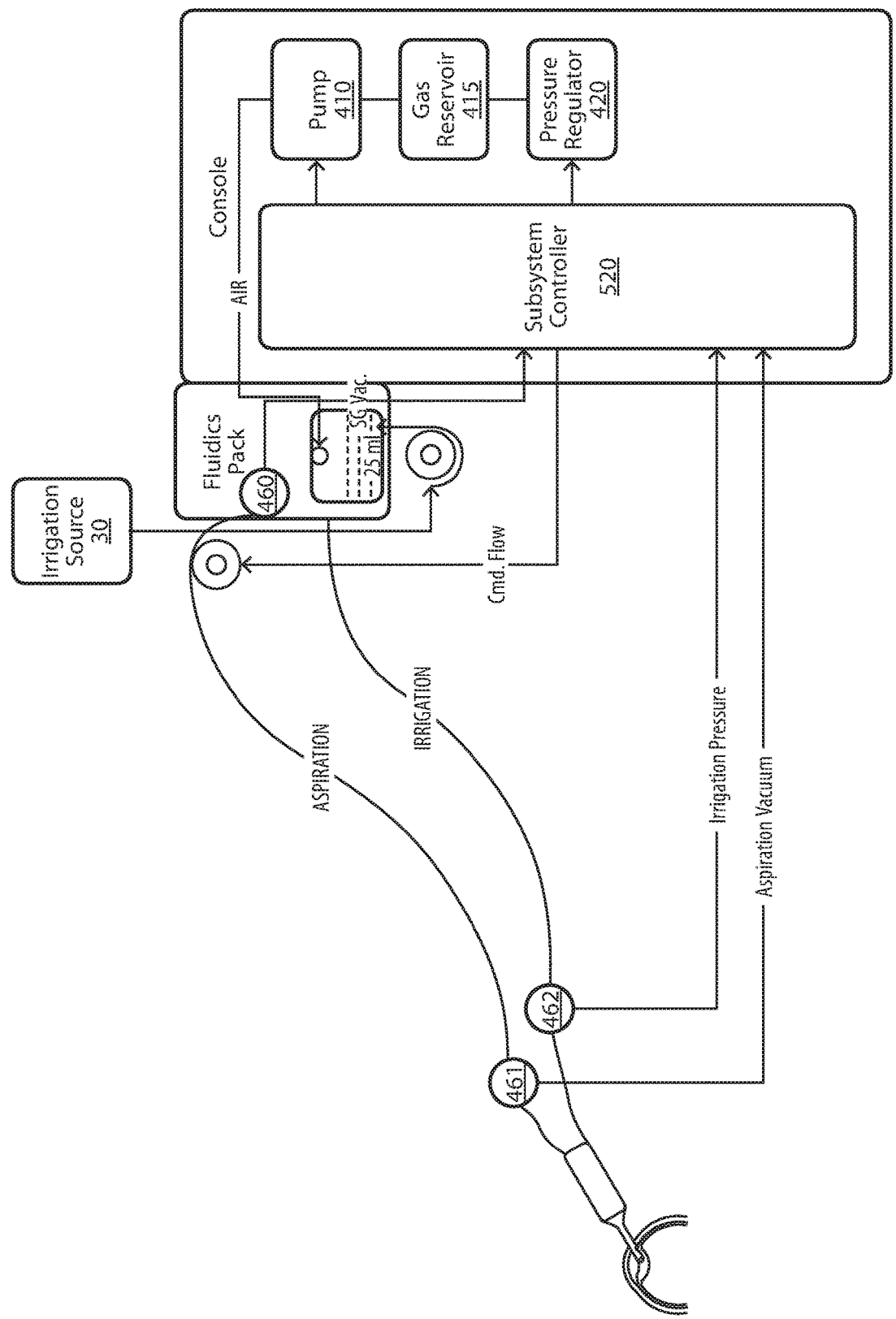
FIG. 5 illustrates an alternative phacoemulsification/diathermy/vitrectomy system and illustrated connected to various components of the system in order to determine characteristics or features of the components.

As illustrated in FIG. 5, the intraoperative pressure management algorithm, which may be resident in surgical console 450, and, more particularly, within subsystem controller 520, may receive sensor data from pressure and/or vacuum sensors 461 and 462, and may continuously measure and adjust the irrigation pressure of system 400 through the subsystem controller 520, in order to maintain the anterior chamber pressure within certain intraoperative parameters. By way of non-limiting example, the intraoperative pressure management algorithm may account for a drop in the anterior chamber pressure due to fluid out flow when the surgeon begins to aspirate fluid via a Command Flow (Cmd. Flow) by pressing on a foot pedal controller (not shown). The subsystem controller 520 may control the pump 410, a gas reservoir 415, and the pressure regulator 420.

In an embodiment of the present invention, the intraoperative pressure management algorithm may measure the difference between sensor 461 and sensor 460 along the aspiration fluid path to calculate actual aspiration flow rate in real-time. This method may be used for both Peristaltic and Venturi based aspiration. The fluid flow between two points of measurement along the aspiration line with a known radius and length may be directly related to pressure difference. Thus, an increase in fluid flow may result in a higher pressure difference between two points and vice versa. Similarly, if the aspiration line is fully or at least partially occluded the pressure difference between two points may approach zero. In an embodiment of the present invention, the intraoperative pressure management algorithm may measure the difference between the two aspiration pressure/vacuum sensors 460 and 461 along the aspiration fluid path to determine the change in intraoperative pressure due to the aspiration outflow. This method may be the same for both Peristaltic and Venturi based aspiration. The fluid flow between two points of measurement along the line with certain radius and length is directly related to pressure difference. Thus, an increase in fluid flow may result in a higher pressure difference between two points and vice versa. When the aspiration line is partially to fully occluded (i.e., restricted to no fluid flow), the pressure difference between two points would approach zero.

In an embodiment of the present invention, occlusion and post occlusion surge detection and mitigation may be obtained through the use of pressure sensors proximate to the surgical site, preferably on the distal end of the handpiece. As discussed above, occlusion and post occlusion surge detection may be detected in both Peristaltic and Venturi based aspiration. By way of example, during aspiration outflow, an occlusion may be created when the handpiece tip is blocked by small fragment of cataract particulate. The blocked tip may cause a vacuum to build in the aspiration line. If the occlusion breaks, the stored the stored energy in the tubing pulls fluid from the anterior chamber. The volume of fluid that the aspiration tubing pulls depends on how much the tubing deformed during the occlusion. This deformation in conjunction with the occlusion itself causes a post occlusion surge in the aspiration line and a drop in intraoperative pressure inside the anterior chamber of the patient's eye.

The algorithm may detect tip occlusions if, for example, the pressure surge is greater than a predetermined occlusion threshold and the current sensor 460 measurement is greater than 90% of maximum set vacuum in both Peristaltic and Venturi based aspiration.

Irrigation Pressure (t) would be set to desired intraoperative pressure established by a user of the phacoemulsification system earlier or prior to the start of surgery. The algorithm may then help detect post occlusion surge if the pressure surge is greater than predetermined post occlusion surge threshold in both Peristaltic and/or Venturi based aspiration.

Irrigation Pressure (t) would be set based on the aspiration outflow established earlier or prior to the start of surgery.

The infusion pressure may be limited to a certain upper bound to ensure that pressure is within acceptable range—an upper bound which may be set by the user of the system. When the occlusion break occurs, the additional infusion flow may help to reduce the drop in the intraoperative pressure, thus providing greater anterior chamber stability.

Similarly, and to prevent errors in pressure control within the system, the present invention may measure system irrigation pressure. As with all programming associated with the surgical console, given the communicative nature of the various microchip inclusive components within the surgical console and those remotely based but in communication with the surgical console, the processing of commands and/or data collected or detected by the system may occur wherever one skilled in the art deems more efficient and/or suitable. The system may provide an alert to a user of the system that the irrigation within the system has been interrupted.

The present invention may also determine if either the irrigation and/or aspiration line has been disconnected to either the handpiece or surgical console. The intraoperative pressure management algorithm may be used to monitor each of the in-line sensors associated with the system and alert the user if, for example, open atmosphere pressure is detected.

In an embodiment of the present invention, both irrigation and aspiration pressure sensors may be placed away from the handpiece. However, propagation delay caused by the tubing length and other characteristics would need to be added into the algorithm. In an embodiment of the present invention, both irrigation and aspiration sensors may be placed inside the fluidics pack to measure the irrigation and/or aspiration pressure during surgery. In an embodiment of the present invention, in-line or non-contact flow sensors may be used to measure the irrigation and/or aspiration flow during surgery. The intraoperative pressure management algorithm may be modified to incorporate data associated with fluid flow changes during surgery.

In an embodiment of the present invention, at least two in-line aspiration pressure sensors may be used to measure the pressure difference along the aspiration fluid path. A first sensor may reside inside the surgical console (e.g., a strain gauge vacuum) and a second sensor may be placed at the distal end of the handpiece on the aspiration connector, for example. These two sensors may measure the aspiration pressure/vacuum real-time during the surgery. The fluid flow between these two points of measurement along a tube having a certain radius and length is directly related to pressure difference. Thus, an increase in fluid flow would result in higher pressure difference between two points and vice versa. As discussed above, when the aspiration line is partially or fully occluded (i.e., near to no fluid flow), the pressure difference between the two sensors would approach zero. The use of the present invention may allow for real-time Venturi aspiration flow determination which may allow the flow to be adjusted as necessary to maintain a stable anterior chamber of the eye during surgery.

In an embodiment of the present invention, a mass air flow sensor may be placed in-line between the Venturi source/regulator and the Venturi output port on the fluid pack manifold. The Venturi fluid flow may be established based on the Venturi air flow changes detected by the mass air flow sensor.

As discussed above, maintaining anterior chamber pressure is of high value to both the patient and the surgeon alike. In an embodiment of the present invention, to maintain anterior chamber pressure in a near-steady state, or at least to keep the anterior pressure within a safe margin above atmospheric pressure, the aspiration flow rate may be limited by using a small inside diameter aspiration line and phacoemulsification tip, or to set the vacuum limit to a lower value. Similarly, the irrigation line flow capability may be increased by raising the irrigation pressure, or increasing the inside diameter of the irrigation line. However, over reducing the inside diameter of the aspiration line and the phacoemulsification tip may cause clogging during phacoemulsification, and may reduce the aspiration vacuum limit which may greatly impact the efficiency of the phacoemulsification procedure. Similarly, raising the IV pole height or otherwise increasing the irrigation pressure may effectively increase irrigation pressure, but such pressure increases may to too long to effectuate. For example, such methods raise pressure at best in a matter of ⅒ of a second, or seconds. Furthermore, increasing the inside diameter of the irrigation line may make priming more difficult.

In an embodiment of the present invention, the system may automatically provide momentary additional irrigation fluid pressure when an occlusion occurs and during an occlusion break by using a mechanism to apply force (pressure) on at least a section of the irrigation path which may contain enough fluid to compensate for the fluid loss experienced in the anterior chamber of the eye during an occlusion break. For example, when the system detects the event of occlusion or occlusion break, a reduced pressure mechanism may apply a pressure to this section in the irrigation path, causing this section to deform, thus momentarily forcing additional irrigation fluid to be supplied to the anterior chamber to compensate for the sudden fluid outflow caused by occlusion break. The applied pressure to the tubing section is intended to generate a momentary fluid pressure, and not to cut off the irrigation flow. In an embodiment of the present invention, the response time of applying the burst of fluid pressure in the irrigation line may be faster than, for example, raising the pressure in the irrigation line by raising the height of the irrigation source and/or adding gas pressure to the irrigation source.

Figure 6:
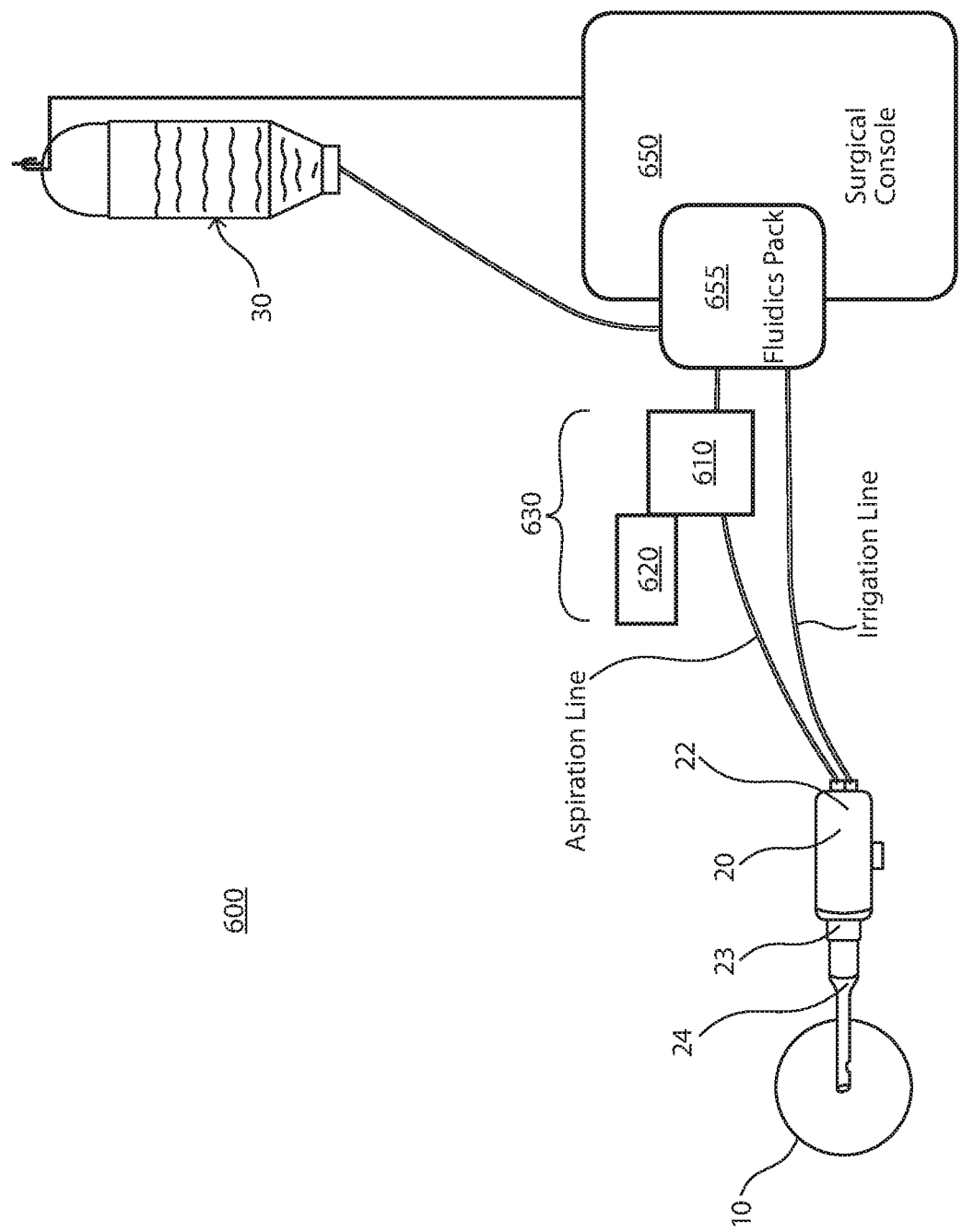
FIG. 6 illustrates an alternative phacoemulsification/diathermy/vitrectomy system and illustrated connected to various components of the system in order to determine characteristics or features of the components.

As illustrated in FIG. 6, the reduced pressure mechanism 630 may be located at any point along an irrigation line between the irrigation source 30 and the handpiece 20. An in-line check valve in series and between reduced pressure mechanism 630 and irrigation source 30 may ensure that pressured fluid moves towards the handpiece 20 and may also prevent fluid back flow from the anterior chamber toward the irrigation source 30 when the mechanism retracts from the activated position to deactivated position, for example. Reduced pressure mechanism 630 may be a single, unitary device, such as a direct action actuator which may exert pressure on the irrigation line by using a plunger or other like apparatus to reduce the interior diameter of the irrigation line sufficiently to force a quantity of irrigation fluid forward through the handpiece 20 into the eye 10. As discussed above, sensors associated with the present invention may allow the surgical console 650 to track and monitor pressure changes associated with occlusions and may activate reduce pressure mechanism 630 as necessary to maintain a desired pressure in the eye 10, and, more specifically, in the anterior chamber of eye 10.

Reduced pressure mechanism 630 may also be composed of multiple parts. For example, reduced pressure mechanism 630 may include an actuation mechanism 620 and a compensation volume module 610. The inclusion of a compensation volume module 610 may allow for an increased volume of irrigation fluid available to the reduced pressure mechanism 630. For example, compensation volume module 610 may include additional amounts of irrigation line which may be acted upon by actuation mechanism 620. Such an increased amount of line may be accommodated by looping the line in a circular pattern and/or weaving the line in a serpentine manner. In any embodiment of line aggregation, those skilled in the art will recognize the various adaptations of actuators and plunger like formations may be made suitable to in part a desired force on at least a portion of the aggregated irrigation line. Similarly, in an embodiment of the present invention, compensation volume module 610 may include a reservoir of irrigation fluid which may be introduced into the irrigation line as necessary to create or augment an increase in pressure. In an embodiment of the present invention, the reduced pressure mechanism 630 and/or in-line check valve may be incorporated into fluid pack 655. In an embodiment of the present invention, fluid pack 655 may be in the form of a cassette which may be removably attached to surgical console 650 and may include at least one reduced pressure mechanism 630 and/or at least one in-line check valve (not shown).

In an embodiment of the present invention, the amount of momentary fluid pressure and the duration of time the applying time of the irrigation source may be adjusted by the reduced pressure mechanism 630 with the amount of pressure and time related to the compensation volume and the speed of the mechanism.

More specifically, the activation of the reduced pressure mechanism 630 may correspond to the detection of the occlusion event by the system and may be deactivated proximate to an indication that the irrigation pressure of the system is recovering. The increased pressure applied by the reduced pressure mechanism 630 significantly reduces the loss of pressure due to an occlusion event and, used alone, may not affect the increase in pressure that might be experienced by the system after compensation for the occlusion event. In an embodiment of the present invention, the use of the reduced pressure mechanism 630 may be included with other aspects of the present invention to improve the reduction in pressure loss and to mitigate any undesired pressure gain after compensation for an occlusion event.

The previous description is provided to enable any person skilled in the art to make or use the disclosed embodiments. Various modifications to these embodiments will be readily apparent to those skilled in the art, and the generic principles defined herein may be applied to other embodiments without departing from the spirit or scope of the invention. Thus, the present disclosure is not intended to be limited to the embodiments shown herein but is to be accorded the widest scope consistent with the principles and novel features disclosed herein.

What is claimed is:

1. A phacoemulsification surgical handpiece comprising:
   a distal end having at least one surgical tool;
   a proximal end having at least one sensor module communicatively connected to at least one irrigation line and at least one aspiration line; and
   at least one sensor located within the at least one sensor module and resident in line with one of the at least one irrigation line, the at least one aspiration line, and the at least one surgical tool; and
   at least one communication module communicatively coupled to the at least one sensor module configured to communicate data indicative of one of the at least one sensor to a surgical console,
   wherein a pressure of one of the at least one irrigation line and the at least one aspiration line is regulated in accordance with the at least one sensor and the at least one sensor module is detachably affixed to the handpiece.

2. The phacoemulsification surgical handpiece of claim 1, wherein the sensor measures one selected from the group consisting of pressure and fluid flow.

3. The phacoemulsification surgical handpiece of claim 1, wherein the at least one sensor is resident in line with each of the at least one irrigation line, the at least one aspiration line, and the at least one surgical tool.

4. The phacoemulsification surgical handpiece of claim 1, wherein the communication module communicates with the surgical console wirelessly.

5. A method for controlling pressure within a surgical system, the method comprising: providing a surgical system, which comprises at least one computing processor capable of accessing code from at least one computing memory associated with the at least one computing processor, the processor in communication with a phacoemulsification surgical handpiece; receiving from the phacoemulsification surgical handpiece data from at least one sensor that is detachably affixed to a proximate end of the phacoemulsification surgical handpiece, the proximate end of the phacoemulsification surgical handpiece having the at least one sensor; and regulating the pressure of at least one fluid line communicatively coupled to the surgical system and the phacoemulsification surgical handpiece in accordance with data from the at least one sensor.

6. The method of claim 5, wherein the at least one fluid line is an aspiration line.

7. The method of claim 5, wherein the at least one fluid line is an irrigation line.

8. The method of claim 5, wherein the surgical system calculates an estimated pressure at the proximate end of the handpiece in accordance with data received from the at least one sensor.

9. The method of claim 5, wherein the sensor measures one selected from the group consisting of pressure and fluid flow.

10. The method of claim 5, wherein the surgical system calculates an estimated surge pressure in accordance with data received from the at least one sensor.

11. The method of claim 10, wherein the surgical system provides a counter pressure to the estimated surge pressure.

* * * * *